United States Patent
Tilse

(10) Patent No.: US 9,788,923 B2
(45) Date of Patent: Oct. 17, 2017

(54) DEVICE FOR DRYING ROOT CANALS

(71) Applicant: Rainer Tilse, Pforzheim (DE)

(72) Inventor: Rainer Tilse, Pforzheim (DE)

( * ) Notice: Subject to any disclaimer, the term of this patent is extended or adjusted under 35 U.S.C. 154(b) by 99 days.

(21) Appl. No.: 14/623,513

(22) Filed: Feb. 17, 2015

(65) Prior Publication Data
US 2015/0157432 A1 Jun. 11, 2015

Related U.S. Application Data

(63) Continuation of application No. PCT/EP2013/066684, filed on Aug. 9, 2013.

(30) Foreign Application Priority Data

Aug. 20, 2012 (DE) .......... 10 2012 107 589

(51) Int. Cl.
*A61C 17/022* (2006.01)
*A61C 17/02* (2006.01)
*A61C 5/40* (2017.01)
*A61C 5/55* (2017.01)

(52) U.S. Cl.
CPC .......... *A61C 17/022* (2013.01); *A61C 5/40* (2017.02); *A61C 5/55* (2017.02); *A61C 17/0202* (2013.01)

(58) Field of Classification Search
CPC ..... A61C 17/022; A61C 17/0202; A61C 5/02; A61C 5/045; A61C 5/55; A61C 5/042
USPC ................. 433/224, 84, 88, 100
See application file for complete search history.

(56) References Cited

U.S. PATENT DOCUMENTS

| | | | |
|---|---|---|---|
| 2004/0107965 A1* | 6/2004 | Hickle | A61M 16/0051 128/204.22 |
| 2007/0248932 A1* | 10/2007 | Gharib | A61C 17/02 433/81 |
| 2008/0145817 A1* | 6/2008 | Brennan | A61C 1/003 433/98 |
| 2011/0003264 A1* | 1/2011 | Cohen | A61C 5/50 433/32 |
| 2011/0111365 A1* | 5/2011 | Gharib | A61C 5/40 433/81 |

(Continued)

FOREIGN PATENT DOCUMENTS

DE 936 591 C 12/1955
DE 10 2005 024 893 A1 8/2006

*Primary Examiner* — Michael Carey
(74) *Attorney, Agent, or Firm* — Hackler Daghighian Martino & Novak

(57) ABSTRACT

A device for drying a root canal includes a cannula configured to inject a gas stream into the root canal. The cannula is a conduit having a proximal end in fluidic communication with a distal end. A handpiece is configured to removably hold the proximal end of the cannula at a distal handpiece end. A gas stream source is connectable to a proximal end of a tube. A distal end of the tube is connectable to the proximal handpiece end. A cut-off valve is disposed within the handpiece in fluidic communication in series between the distal handpiece end and the proximal handpiece end. The cut-off valve is configured to cut off the gas stream flowing through the handpiece. A manually-controlled operating element is mechanically coupled to the cut-off valve, where the operating element is configured to be controlled by a dentist or technician holding the handpiece.

18 Claims, 2 Drawing Sheets

(56) References Cited

U.S. PATENT DOCUMENTS

2012/0034579 A1* 2/2012 Schoeffel ................ A61C 5/02
                                                        433/224
2014/0234795 A1* 8/2014 Holbeche ........... A61C 17/0202
                                                         433/27

* cited by examiner

DEVICE FOR DRYING ROOT CANALS

CROSS-REFERENCE TO RELATED APPLICATIONS

This continuation application claims priority to PCT/EP2013/066684 filed on Aug. 9, 2013 which has published as WO 2014/029638 A3 and also the German application number 10 2012 107 589.1 filed on Aug. 20, 2012 and published as DE 10 2012 107 589 A1, the contents of which are fully incorporated herein with these references.

DESCRIPTION

Field of the Invention

The invention relates to a dental instrument for drying a root canal.

Background of the Invention

Drying of root canals is an important step in a dental root canal treatment. Moisture in the root canal provides a biosphere for bacteria and makes it difficult for the root filling paste to adhere.

In a root canal treatment, the root canal is cleaned mechanically and with various aqueous rinsing solutions. Then the root canal must be dried. To do so, paper tips are usually introduced into the root canal to absorb the liquid. This is repeated until the paper tips are no longer moist. The root canal should be as dry and sterile as possible. The root filling is introduced in the next step.

An object of the present invention is to show how the work of drying root canals can be facilitated for dentists.

This object is achieved by a device having the features defined in the independent claims. Advantageous refinements of the invention are the subject matter of dependent claims.

SUMMARY OF THE INVENTION

A device according to the invention for drying a root canal has a cannula for injecting a stream of gas into the root canal, a handpiece for holding the cannula and a safety valve to prevent an increase in the gas pressure in the cannula beyond a critical threshold level. The device may also be referred to as a system for drying a root canal because several components must be linked together, namely the handpiece and cannula, to dry a root canal.

By injecting a stream of gas, it is possible to dry a root canal conveniently and thoroughly. With the device according to the invention, a root canal treatment is greatly facilitated for dentists.

The handpiece can be connected by means of a tube to a source of the gas stream, for example, a pump or a compressed gas container. A dentist's treatment chair has extensive equipment, which usually also includes a pump. The handpiece for connection to such equipment may be provided by attaching it to the end of a tube, for example. However, the device according to the invention may also have a separate pump, to which it can be connected by means of a tube.

The device has a safety valve to prevent the gas pressure in the cannula from rising beyond a predefined threshold level. At a high pressure, injected gas can penetrate through the root tip into periapical tissue, where it can cause damage. A cannula introduced into the root canal may, under some circumstances, occlude the root canal to such an extent that the gas stream can escape from the root canal along the outside of the cannula only to an inadequate extent. In order for this not to lead to a dangerous increase in pressure, a device according to the invention has a safety valve, which limits the pressure in the cannula and thus also in the root canal to a safe level from the standpoint of dentistry. The safety valve is preferably an excess pressure valve, which opens as soon as the gas pressure has reached a predefined threshold level and then allows the gas stream to pass by the cannula, for example, through an opening in the handpiece, which is provided for this purpose. The safety valve is preferably installed in the handpiece. However, a safety valve can also be integrated into the cannula, for example, in the form of a rupture disk. A subarea of the lateral surface in a section of the cannula that is not provided for insertion into the root canal may be designed to be so thin that the cannula ruptures there as soon as the pressure in the cannula exceeds a predefined threshold level. A safety valve integrated into the cannula may thus be designed as a weakened wall area of the cannula. This wall area may be provided at such a great distance from the end that is inserted into the root canal for drying that the weakened wall area remains outside of the root canal and gas can escape from a cannula with no problem in the event of rupture of this wall area.

The cannula may be designed as a small hose or as a tube. A cannula in the form of a hose or flexible tube has the advantage that it can be adapted in a flexible manner to the spatial conditions in a patient's mouth and therefore can be inserted more easily into a root canal. The cannula is preferably made of metal, for example, a nickel-titanium alloy, but it may also be made of plastic, for example. Cannulas made of superelastic alloys such as Nitinol, for example, or other nickel-titanium alloys can be manufactured as hoses that are very flexible.

The cannula is preferably attached replaceably to the handpiece. For example, the handpiece may have an opening into which the cannula is inserted. The cannula can then be replaced advantageously after each treatment to prevent hygiene problems. One aspect of the present invention is therefore also a cannula as a disposable part of a device according to the invention and/or a system according to the invention.

Air or another gas, for example, nitrogen or oxygen, may be used for the gas stream. Oxygen is available inexpensively in a technical-grade purity and has the advantage of destroying anaerobic microorganisms, such as those which often occur in root canals. An air stream can be created by means of a pump, which is designed as part of the device according to the invention or is an external device to which the device according to the invention is connected. The device according to the invention may be connected to a pump, for example, which is installed in a dental treatment chair.

If the gas stream is taken from a compressed gas container, i.e., for example, if nitrogen is injected into the root canal, then it is possible to create a very dry gas stream advantageously without any additional measures, such that it contains hardly any moisture and consequently can dry the root canal rapidly and particularly well.

Another advantageous refinement of the invention provides that the device has an electric heating element for heating the gas stream. A heated gas stream can take up moisture better and therefore can dry a root canal faster. The heating element may be part of the handpiece or, for example, may heat the tube through which the gas stream is supplied to the handpiece. Tubes can be heated efficiently with a heating wire, in particular using a coiled heating wire.

A device according to the invention preferably has a control circuit for regulating the temperature of the gas stream at an ideal value. Overheating of the gas stream, which could lead to damage to the root canal or the periapical tissue, can be prevented by a control circuit. The control circuit may be constructed with a temperature sensor, for example, a measurement resistor, and a regulator, for example, in the form of a microprocessor.

The ideal temperature of the gas stream may be fixedly preset by the manufacturer at 42° C., for example. The ideal temperature may also be adjustable by the user. An operating element, for example, in the form of a turn knob or a pushbutton, may be provided for this purpose. The operating element is preferably part of the handpiece.

An ideal temperature value in the range of 37° C. to 42° C., in particular in the range of 40° C. to 42° C., is particularly advantageous because an elevated temperature also causes a reduction in the microbe count. It is advantageous in particular if the temperature of the gas stream is 42° C., because a definite reduction in the microbe count is achieved in the root canal although no tissue damage need be feared at this temperature.

Another advantageous refinement of the invention provides that the cannulas have lateral openings for gas to escape. The cannula is a tube or hose, for example, having openings in the lateral surface. If the cannula has only a single outlet opening, namely at its end, it may happen that this opening is blocked in the root canal and then no more gas can escape. However, in the case when a cannula has a plurality of gas outlet openings, it is very unlikely that the gas outlet will be obstructed.

Another advantageous refinement of the invention provides that the outside of the cannula has recesses and/or protrusions. This measure reduces the risk of a root canal being obstructed due to a cannula inserted into it to such an extent that injected gas can no longer escape from the root canal along the outside of the cannula. Protrusions, for example, nubs or recesses, for example, grooves can ensure that the cannula is not in tight contact with the inside of the root canal on all sides.

Another advantageous refinement of the invention provides that the cannula has length markings, for example, lines running across its longitudinal direction. The length markings can be at predefined intervals from the end of the cannula, which is inserted into a root canal during drying. These length markings make it easier for the dentist to recognize how far the cannula has been inserted into the root canal at the moment. Such length markings are usually also provided on instruments for cleaning root canals and are sometimes also referred to as distance markings because they mark the distance from the end of the instrument.

Another advantageous refinement of the invention provides for a gas drying device. For example, the air stream to be injected may be passed through a chamber filled with a desiccant before being introduced into the cannula. As the amount of moisture contained in the injected gas stream is smaller, its drying of the root canal is better.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention.

DETAILED DESCRIPTION OF THE PREFERRED EMBODIMENTS

Figure 1:
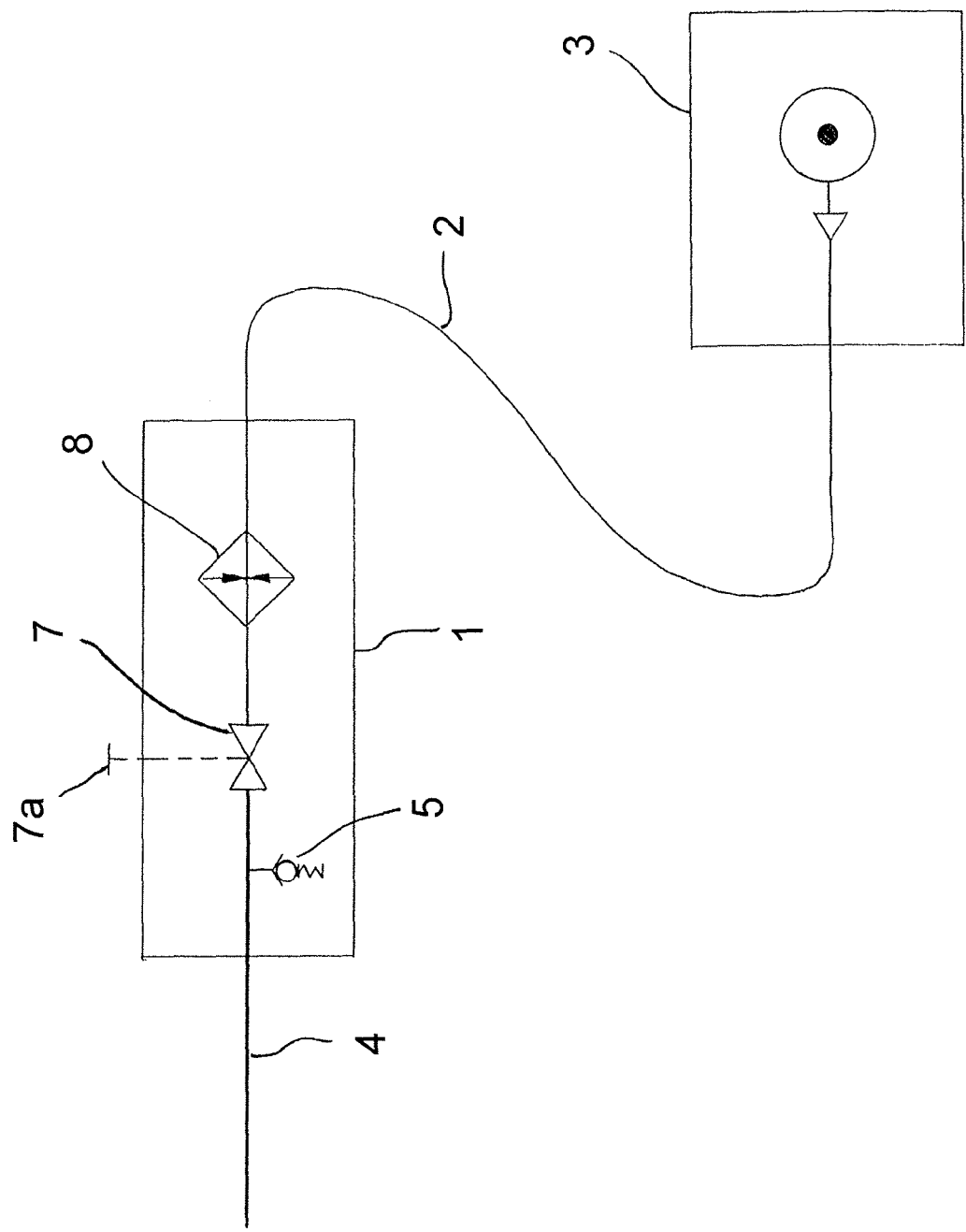
FIG. 1 shows a schematic diagram of a device for drying a root canal.

With the device shown in FIG. 1, it is possible to dry a root canal by injecting a stream of gas. This device therefore has a handpiece 1, which can be connected by a tube 2 to a pump 3 or some other source of a gas stream, for example, a compressed gas container. The handpiece 1 has a cannula 4, which can be inserted into a root canal. The cannula 4 may be inserted into the handpiece 1, for example, and held there by clamping, so that it can be replaced easily.

The handpiece 1 has a safety valve 5. As soon as the pressure of the gas stream in the handpiece 1 has reached a critical threshold level, the safety valve 5 opens. When the safety valve 5 is open, gas can escape through an opening in the handpiece 1 provided for this purpose. In this way the safety valve 5 prevents the gas pressure in the handpiece 1 and/or in the cannula 4 and therefore in a root canal from rising above a predefined threshold level. This is important because on insertion of the cannula 4 into a tight root canal there is the risk that the gas stream injected into it can no longer escape from the root canal by passing along the outside of the cannula 4 and therefore the gas pressure rises. At a high pressure, injected gas can penetrate through the root tip into periapical tissue. This risk is counteracted by the safety valve 5. The safety valve 5 may be spring loaded.

The handpiece 1 additionally includes a cut-off valve 7 which allows a gas stream to flow through or blocks it depending on the switch setting. The cut-off valve 7 may be operated by a user by means of an operating element 7a. The cut-off valve 7 is arranged upstream from the safety valve 5. The cut-off valve 7 contains a spring, which resets it into its closed position when the operating element 7a, for example, a pushbutton, is not being operated and/or pressed (any longer).

In the illustrative embodiment shown here, the handpiece 1 includes an electric heating element 8 for heating the gas stream, for example, a PTC element which has a sudden increase in its electric resistance at a critical temperature. However, a heating element may also be integrated into the pump 3, for example, or mounted on the tube 2 connecting the pump 3 to the handpiece 1.

The gas stream, which may be an air stream in the simplest case, is regulated at a set temperature by a control circuit. A temperature sensor for measuring the gas temperature may be arranged in the handpiece 1, the tube 2 or the pump 3.

The set temperature may be fixedly predetermined by the manufacturer or may be adjustable by the user, for example, with an operating element on the handpiece 1. Set temperatures in the range of 37° C. to 42°, in particular 42° C., are advantageous. A reduction in the microbial population in the root canal can be achieved with a gas stream at such a temperature without any risk of damage or injury to the tissue due to the influence of the temperature.

To increase the drying effect of the gas stream, a gas-drying device may be provided. A simple gas drying can be achieved by exposing the gas stream to a desiccant, for example, silica gel or some other hygroscopic chemical. For example, the pump 3 or the handpiece 1 may have a chamber which is provided for accommodating the desiccant and through which the gas flow passes. The gas-drying device may also be more complex, for example, in that an air stream is first cooled to condense the moisture contained therein and only then is conveyed by the pump 3 to the handpiece 1.

Figure 2:
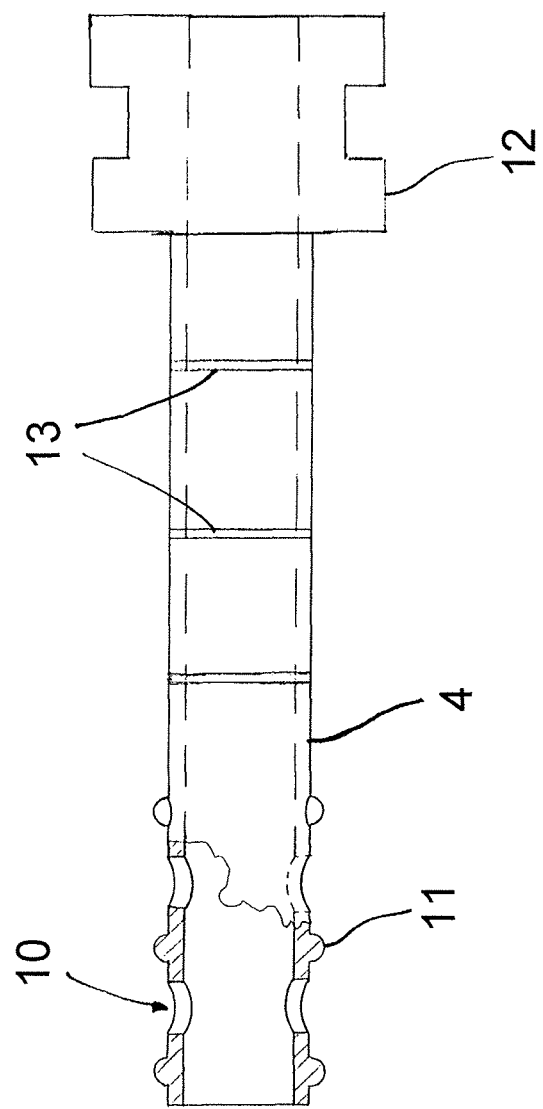
FIG. 2 shows a cannula of this device in a longitudinal section.

FIG. 2 shows an illustrative embodiment of the cannula 4 to be inserted into the handpiece 1. The cannula 4 is a tube made of a superelastic alloy, for example, Nitinol. Superelastic alloys are often referred to in the literature as shape memory alloys.

The cannula 4 has lateral gas outlet openings 10. An injected gas stream can therefore escape from the jacket surface not only at the end of the cannula 4 but also on its lateral surface. On the outside the cannula 4 has a plurality of protrusions 11, for example, in the form of nubs. If the cannula 4 when it is inserted into a root canal, the protrusions 11 act as spacers and ensure that a clearance through which the inject gas stream can escape from the root canal remains between the outside of the cannula and the inside of the root canal. The same effect can be achieved with recesses on the outside of the cannula 4, for example, grooves.

The cannula 4 has a connecting section 12 for fastening the cannula 4 in a handpiece 1 on one end. The connecting section 12 preferably has an undercut. The connection section may be designed for a bayonet closure, for example.

The cannula 4 has length markings 13, for example, in the form of peripheral rings which are mounted at predetermined intervals from the free end of the cannula. During the treatment, the dentist can read on these length markings how far the cannula has been inserted into a root canal. Furthermore the cannula may have a mark, for example, a color mark which indicates the thickness of the cannula. If cannulas of different thicknesses are used in root canals of different sizes are provided there, a mark permits a simple differentiation of various cannulas.

The cannula 4 may taper toward its free end. This is advantageous because root canals may also taper.

Although several embodiments have been described in detail for purposes of illustration, various modifications may be made to each without departing from the scope and spirit of the invention. Accordingly, the invention is not to be limited, except as by the appended claims.

What is claimed is:

1. A device for drying a root canal, comprising:
   a cannula configured for injecting a gas stream into the root canal; and
   a handpiece configured for holding the cannula, wherein the handpiece has a safety valve configured to prevent the gas pressure in the cannula from increasing above a predefined threshold level, wherein the safety valve is spring loaded.

2. The device according to claim 1, further comprising an electric heating element configured for heating the gas stream.

3. The device according to claim 2, further comprising a control circuit for regulating the temperature of the gas stream at a setpoint value.

4. The device according to claim 3, further comprising at least one operating element for adjusting the setpoint value.

5. The device according to claim 1, wherein the cannula has lateral openings for the gas stream to escape.

6. The device according to claim 1, wherein the handpiece has a cut-off valve for cutting off the gas stream.

7. The device according to claim 1, further comprising a gas drying device.

8. The device according to claim 1, wherein the cannula is mounted replaceably on the handpiece.

9. The device according to claim 1, wherein an outside of the cannula has recesses and/or protrusions.

10. A cannula configured for injecting a gas stream into a root canal, wherein the cannula has lateral openings for the gas to escape wherein an outside of the cannula has protrusions.

11. The cannula according to claim 10, further comprising length markings which are arranged at predetermined distances from a distal end of the cannula which is inserted into a root canal for drying.

12. A device for drying a root canal, comprising:
    a cannula configured to inject a gas stream into the root canal, the cannula comprising a conduit having a proximal end in fluidic communication with a distal end; a handpiece configured to removably hold the proximal end of the cannula at a distal handpiece end, wherein the distal handpiece end is in fluidic communication with a proximal handpiece end;
    a gas stream source connectable to a proximal end of a tube, wherein a distal end of the tube is connectable to the proximal handpiece end;
    the handpiece having a vent that is in fluidic communication with the distal handpiece end and the proximal handpiece end, said vent being closed by a safety valve that is configured to open when gas pressure in the handpiece reaches a predefined threshold level thereby reducing gas pressure in the cannula, wherein the safety valve is spring loaded.

13. The device of claim 12, including a plurality of lateral openings disposed at the distal end of the cannula configured to allow the gas stream to escape.

14. The device of claim 12, including a cut-off valve disposed within the handpiece in fluidic communication in series between the distal handpiece end and the proximal handpiece end, and a manually-controlled operating element mechanically coupled to the cut-off valve, the operating element configured to be controlled by a dentist or technician.

15. The device of claim 14, including a gas drying device configured to remove moisture from the gas stream, wherein the gas drying device is coupled to either the gas stream source, tube or handpiece.

16. The device of claim 15, including an electric heating element configured to heat the gas stream, wherein the electric heating element is coupled to either the gas stream source, tube or handpiece.

17. The device of claim 16, including a plurality of length markings arranged at predetermined distances along the distal end of the cannula, the plurality of length markings configured to show a depth of cannula insertion into the root canal.

18. The device of claim 17, including a control circuit connected to the electric heating element, the control circuit configured to regulate the temperature of the gas stream at a setpoint value.

* * * * *